US011427796B2

(12) United States Patent
Bernard et al.

(10) Patent No.: US 11,427,796 B2
(45) Date of Patent: Aug. 30, 2022

(54) BIOREACTOR FOR THE SELECTION OF MICROALGAE

(71) Applicants: INRIA INSTITUT NATIONAL DE RECHERCHE EN INFORMATIQUE ET EN AUTOMATIQUE, Le Chesnay (FR); CENTRE NATIONAL DE LA RECHERCHE SCIENTIFQUE (C.N.R.S), Paris (FR); UNIVERSITE NICE SOPHIA ANITPOLIS, Nice (FR)

(72) Inventors: Olivier Bernard, Carros (FR); Hubert Bonnefond, Nice (FR); Antoine Sciandra, Villefranche sur Mer (FR); Éric Pruvost, Nice (FR); Ghjuvan Grimaud, Ajaccio (FR)

(73) Assignee: Inria Institut National De Recherche En Informatique Et En Automatique, Le Chesnay (FR)

( * ) Notice: Subject to any disclaimer, the term of this patent is extended or adjusted under 35 U.S.C. 154(b) by 236 days.

(21) Appl. No.: 16/335,390

(22) PCT Filed: Sep. 19, 2017

(86) PCT No.: PCT/FR2017/052510
§ 371 (c)(1),
(2) Date: Mar. 21, 2019

(87) PCT Pub. No.: WO2018/055282
PCT Pub. Date: Mar. 29, 2018

(65) Prior Publication Data
US 2019/0284516 A1 Sep. 19, 2019

(30) Foreign Application Priority Data

Sep. 21, 2016 (FR) ...................................... 1658863

(51) Int. Cl.
*C12M 3/00* (2006.01)
*C12M 1/00* (2006.01)
(Continued)

(52) U.S. Cl.
CPC ............ *C12M 21/02* (2013.01); *C12M 31/02* (2013.01); *C12M 35/00* (2013.01); *C12M 41/06* (2013.01);
(Continued)

(58) Field of Classification Search
CPC .......... C12M 21/02; C12M 41/12; C12N 1/12
See application file for complete search history.

(56) References Cited

U.S. PATENT DOCUMENTS

| 2009/0148931 A1* | 6/2009 | Wilkerson | .............. | F24S 23/12 |
| | | | | 435/286.1 |
| 2012/0178123 A1* | 7/2012 | Rosen | ................... | C12M 47/10 |
| | | | | 435/42 |

(Continued)

FOREIGN PATENT DOCUMENTS

| EP | 0554162 A1 | 8/1993 |
| WO | 2010036334 A1 | 4/2010 |

(Continued)

OTHER PUBLICATIONS

Database WPI, XP-002769650, Thomson Scientific, 2015.

*Primary Examiner* — Nathan A Bowers
(74) *Attorney, Agent, or Firm* — Maynard Cooper & Gale, P.C.; Brian T. Sattizahn

(57) ABSTRACT

The invention relates to a bioreactor comprising a tank (100) capable of being operated for a working period, said tank (100) being intended to receive a culture medium comprising a cellular culture of photosynthetic microorganisms, a light source (200) arranged to emit incident light having a chosen incoming light intensity (Iin) in the direction of the
(Continued)

tank, a temperature probe (400) for measuring the temperature of said culture medium in the tank, and a temperature regulator (500) capable of raising and lowering the temperature of said culture medium in the tank, and further comprising a control (700) of the temperature regulator arranged to adjust the temperature of the culture medium to a low setpoint value (VCB) during a first period, and to adjust the temperature of the culture medium to a high setpoint value (VCH) during a second period, the succession of said first and second periods making it possible to induce a cellular stress in at least some of said photosynthetic microorganisms during the working period.

16 Claims, 6 Drawing Sheets

(51) Int. Cl.
| | | |
|---|---|---|
| *C12M 1/34* | (2006.01) | |
| *C12N 5/00* | (2006.01) | |
| *C12M 1/36* | (2006.01) | |
| *C12N 1/12* | (2006.01) | |
| *C12M 1/42* | (2006.01) | |

(52) U.S. Cl.
CPC ............ *C12M 41/12* (2013.01); *C12M 41/36* (2013.01); *C12M 41/48* (2013.01); *C12M 47/06* (2013.01); *C12N 1/12* (2013.01); *C12N 5/0018* (2013.01)

(56) References Cited

U.S. PATENT DOCUMENTS

| | | | |
|---|---|---|---|
| 2013/0078708 A1* | 3/2013 | Roux Dit Buisson | C12M 41/12 435/257.1 |
| 2015/0322392 A1* | 11/2015 | Mars | C12M 23/58 435/292.1 |
| 2016/0281044 A1* | 9/2016 | Laustsen | C12M 21/14 |

FOREIGN PATENT DOCUMENTS

| | | |
|---|---|---|
| WO | 2011035042 A2 | 3/2011 |
| WO | 2015121987 A1 | 8/2015 |
| WO | 2015140467 A1 | 9/2015 |

\* cited by examiner

BIOREACTOR FOR THE SELECTION OF MICROALGAE

The present invention relates to a bioreactor capable of inducing a cellular stress on microalgae cells by means of temperature variations. The invention also relates to a method for selecting microalgae based on a cellular stress induced by temperature variations.

Both prokaryotic and eukaryotic photosynthetic microorganisms exist, which are grouped together under the term "microalgae". Prokaryotic photosynthetic microorganisms are represented by cyanobacteria (sometimes referred to as "blue-green algae"). Eukaryotic photosynthetic microorganisms are represented by a multitude of classes, among which mention may be made of Chlorophyceae, diatoms, Chrysophyceae, Coccolithophyceae, Euglenophyceae and Rhodophyceae. In general, the size of a microalgae cell is between 1 μm and 100 μm.

Current estimates suggest that there are more than a million species of microalgae, of which several tens of thousands of species are catalogued. Microalgae are ubiquitous and they are found equally in fresh water, brackish water and seawater.

Microalgae production is a fast-growing sector. This is because microalgae synthesize numerous products of different natures, among which mention may be made of proteins, antioxidants, pigments, and the long-chain polyunsaturated fatty acids DHA (docosahexaenoic acid) and EPA (eicosapentaenoic acid).

Thus, microalgae have applications in several technological fields and in particular in the cosmetics industry, the pharmaceutical industry, aquaculture, or the functional food or food supplement industry.

Furthermore, microalgae are used in the production of bioenergy. Microalgae have a capacity to capture light energy in order to fix and metabolize inorganic carbon from carbon dioxide ($CO_2$) in energy molecules. The coupling of microalgae with $CO_2$ and the fact that microalgae are often rich in sugars or in oils means that microalgae are of great benefit in the production of biofuels. This coupling is also responsible for the purifying capacities possessed by microalgae.

Microalgae are photosynthetic species. The cells of microalgae need light in order to proliferate. Microalgae may be cultured using natural light (sunlight) or artificial light. There are open culture systems of the culture pond type (also referred to as "raceway" pond), and closed culture systems such as batch bioreactors, fed-batch bioreactors or continuous bioreactors.

In general, all the culture systems have a tank intended to receive a culture medium which comprises nutrients. The microalgae are dispersed in this culture medium and receive light at a fixed temperature or at a variable temperature depending on the natural climatic conditions.

Ideally, the temperature is generally chosen close to the temperature of the natural environment of the microalgae. This allows a good growth rate of the cells. However, this can sometimes only be done with difficulty, or is expensive.

In the culture systems for microalgae, light plays an important role for growth. In simple terms, the more the microalgae absorb light, the more this promotes their growth. However, in the prior art systems, the light is predominantly absorbed by the cells close to the light source. When the density of microalgae is high, a large part of the light does not manage to penetrate deeply into the tank. Consequently, the microalgae deep in the tanks are in the dark and cannot proliferate correctly. The culture systems thus have a problem of overexposure to light of the cells close to the light source and a problem of underexposure of the cells located at depths in the culture medium. This light gradient within the culture systems limits the production of microalgae. Thus, the light source and the light intensity are limiting factors for production methods.

The prior art proposes an approach which consists in genetically modifying the microalgae. This involves reducing the size or the number of the light-harvesting complexes (chlorophyll molecules) and/or modifying the ratios between the various pigments (in particular chlorophyll a, chlorophyll b, chlorophyll c, carotenoids and other pigments) of the microalgae, in order to make them more transparent.

Document WO 2014/089533 discloses mutant microalgae having reduced light-harvesting complexes. Each microalgae cell captures a smaller amount of light, thereby enabling the light to penetrate deeply into the tanks. The cells located in the regions furthest from the light source are therefore less shaded. However, this approach requires complex and expensive processes of genetic engineering or of mutation-selection, such as chemical mutagenesis or treatment by ultraviolet or gamma irradiation. Moreover, the culture systems only comprise a single type of mutant: these are microalgae monocultures. The monocultures are less robust, in particular in the face of industrial exploitation conditions.

The problems linked to the light gradient within culture systems remain limiting factors in production methods, and most particularly in systems for maximizing biomass production. The need to improve the yield of culture systems persists.

The prior art proposes, moreover, culture systems in which microalgae are specifically selected for increasing the production yield.

WO 2013/012329 discloses a method for selecting microalgae having an increased capacity for storing components that are of use for producing biofuels. A culture of various strains of microalgae is subjected to nutritional stress. Only the strains capable of storing a high concentration of nutrients survive this stress. The strains are then harvested and cultured in the culture systems described above.

However, the number of strains that can survive a nutritional stress is limited. Furthermore, the need to culture microalgae in an environment that simulates the temperatures of a natural microalgae environment requires an adaptation from one strain to another. This is accompanied by a heating/cooling program which means high costs and high energy losses.

The present invention aims to improve the situation.

To this purpose, the invention will introduce a bioreactor comprising a tank capable of being operated for a working period, said tank being intended to receive a culture medium comprising a cell culture of photosynthetic microorganisms, a light source arranged to emit incident light having a chosen incoming light intensity in the direction of the tank, a temperature probe for measuring the temperature of said culture medium in the tank, and a temperature regulator capable of increasing and decreasing the temperature of said culture medium in the tank. The bioreactor of the invention also comprises a control of the temperature regulator arranged to adjust the temperature of the culture medium to a low setpoint value during a first period, and to adjust the temperature of the culture medium to a high setpoint value during a second period, the succession of said first and second periods making it possible to induce a cellular stress in at least some of the photosynthetic microorganisms during the working period.

In one embodiment, the bioreactor also comprises a light sensor facing the light source, the sensor being capable of measuring an outgoing light intensity and of transmitting data relating to this intensity to the controller in order to calculate the concentration of the cell culture and to operate the tank at said chosen cell culture concentration in the culture medium during the working period.

In another embodiment, the bioreactor also comprises a controller arranged to operate the tank at a chosen cell culture concentration ($x_i$), preferably at a concentration substantially less than or equal to 1.0 g/l, in the culture medium during the working period.

The consequence of the stress induced on the cells is a selection and/or adaptation of the cell culture of photosynthetic microorganisms (microalgae). Only the strains capable of surviving the stress are harvested after the method of the invention (that is to say preferably after several successive working period cycles). The strains harvested have valuable properties (in particular increased lipid storage capacities or increased synthesis of lipids of industrial interest).

In one embodiment, the control is arranged to determine the low setpoint value and said high setpoint value and said first and second periods so as to maintain a mean setpoint value $V_M$ during the working period. In this embodiment, the mean setpoint value $V_M$ is equal to the sum of the product of said low setpoint value and of said first period and of the product of said high setpoint value and of said second period, divided by the working period:

$$VM = \frac{(\text{low setpoint value} \times \text{first period}) + (\text{high setpoint value} \times \text{first period})}{\text{working period}}$$

This makes it possible to induce a controlled stress on the cell culture during the working period. The adaptation and/or selection of the microalgae is carried out while avoiding excessive cellular degradation or cell death.

The algae cells acclimatize to the mean setpoint temperature. The working period can be repeated several times. Each working period can redefine a mean setpoint value $V_M$. Consequently, during each working period, the algae cells can acclimatize to a new mean setpoint temperature. According to one embodiment, the mean setpoint value $V_M$ is increased over the course of successive working periods. According to another embodiment, the mean setpoint value $V_M$ is decreased over the course of successive working periods. Thus, the algae cells acclimatize to a respectively increasingly high and increasingly low mean temperature.

The mean setpoint value may be substantially equal to the optimal growth temperature ($T_{opt}$) of the cell culture of photosynthetic microorganisms. The adaptation and/or the selection of the microalgae is therefore carried out around optimal growth temperature. This embodiment takes into account the sensitivity of the microalgae and their natural evolution environment. This further avoids excessive cellular degradation or cell death.

The chosen incoming light intensity $I_{in}$ of the incident light is preferably fixed during the working period. This avoids excessive stresses induced by virtue of light variations. The incoming light intensity may be between 100 and 2000 µmol quanta $m^{-2}$ $s^{-1}$. The higher the concentration of the cell culture in the culture medium, the higher the adjustment of the light intensity. This allows good scattering of the light within the tank of the bioreactor. Advantageously, the incoming light intensity is equal to approximately 250 µmol quanta $m^{-2}$ $s^{-1}$. This allows good operation at a chosen cell culture concentration $x_i$ in the culture medium substantially equal to 1.0 g/l. Under these conditions, the scattering of light within the tank and the nutritional conditions of the culture medium can be easily controlled. This results in a good growth rate and thus a good general yield.

In one embodiment, the working period is equal to 24 hours, and the first period is equal to 8 hours and the second period is equal to 16 hours. This application scheme for the low and high setpoint values allows good adaptation of the microalgae cells. Preferably, the working period is repeated once it has been completed. This makes it possible to engage a further selection cycle. After several repetitions, the selection and/or adaptation of the cells is striking. According to one embodiment, the working period is repeated 7 to 360 times.

In one preferential embodiment, the control is arranged to receive data relating to the growth rate of the cell culture of photosynthetic microorganisms after one or more working periods. After reception, the control fixes the low setpoint value and said high setpoint value after said reception of the data relating to the growth rate of said cell culture of photosynthetic microorganisms. The data relating to the growth rate of the cell culture indicate whether or not it is in a growth situation. When the growth stagnates, the temperature variation scheme is not modified so as to allow the microalgae cells to adapt to the climatic conditions. When the cell culture is growing, the temperature variation scheme is made more strict: the difference between the low and high setpoint values is increased. Only the cells capable of adapting to the new, more extreme climatic conditions survive. This makes it possible to increase the selection and/or adaptation criteria and thus to harvest final strains having improved properties. The final strains are of great industrial value.

The invention is also directed toward a method for selecting photosynthetic microorganisms, comprising the following steps:
1. Providing a bioreactor as described above;
2. Filling the tank with a culture medium;
3. Inoculating the culture medium with a cell culture consisting of photosynthetic microorganisms;
4. Operating the tank during a working period, preferably at a chosen cell culture concentration $x_i$ in the culture medium, and adjusting the incoming light intensity to a chosen value;
5. Adjusting the temperature of the culture medium to a low setpoint value ($V_{LS}$) during a first period, and adjusting the temperature of the culture medium to a high setpoint value ($V_{HS}$) during the second period, the succession of said first and second periods making it possible to induce a cellular stress in at least some of said photosynthetic microorganisms during the working period;
6. Harvesting the photosynthetic microorganisms.

The low setpoint value and the high setpoint value and the first and second periods are adjusted so as to maintain a mean setpoint value ($V_M$) during the working period, the mean value being equal to the sum of the product of said low setpoint value and of said first period and of the product of said high setpoint value and of said second period, divided by the working period:

$$VM = \frac{(\text{low setpoint value} \times \text{first period}) + (\text{high setpoint value} \times \text{first period})}{\text{working period}}$$

The mean setpoint value may be substantially equal to the optimal growth temperature ($To_pt$) of the cell culture of photosynthetic microorganisms. In another embodiment, the mean value is chosen to meet a biologically acceptable temperature criterion specific to a chosen microalgae strain. In other words, the mean setpoint value can take any temperature that is biologically acceptable for the microalgae strain(s) present in the tank.

The working period may be equal to 24 hours. The first period is then preferably equal to 8 hours and the second period is then equal to 16 hours.

In general, for a given (predefined) working period, the second period lasts twice as long (double) as the first period.

The temperature adjustment step 5. is advantageously repeated 2 to 360 times. This increases the selection and/or adaptation criterion.

The method of the invention may also comprise the following steps:
4a. Taking a portion of the culture medium comprising at least one portion of said photosynthetic microorganisms; and
4b. Compensating for said portion of the culture medium comprising at least one portion of said photosynthetic microorganisms that is taken, with fresh culture medium.

Preferably, the temperature adjustment step 5. is repeated more than 2 times so as to bring about a cellular degradation of at least one portion of said photosynthetic microorganisms and thus select the photosynthetic microorganisms having valuable properties.

The harvesting step 6. is preferably carried out when the culture medium comprises a cell culture of photosynthetic microorganisms consisting of more than 75%, preferentially more than 90%, even more preferentially substantially 100% of photosynthetic microorganisms having valuable properties. In one embodiment, the method of the invention also comprises the following steps:
7. Inoculating a fresh culture medium with the modified photosynthetic microorganisms harvested in step 6. in a bioreactor; and
8. Operating the bioreactor of step 7. for a production of biomass consisting of said modified photosynthetic microorganisms.

This makes it possible to culture the strains harvested at the end of step 6. for an industrial exploitation.

According to one preferential embodiment, the temperature adjustment step 5. is repeated 2 to 360 times. In this embodiment, at each repetition, the control receives data relating to the growth rate of the cell culture of photosynthetic microorganisms after one or more working periods. The control then fixes the low setpoint value and said high setpoint value after this reception of the data relating to the growth rate, in the following way:
When the growth rate is less than or equal to zero:
the low setpoint value and the high setpoint value remain unchanged for the next working period (or cycle).
When the growth rate is greater than zero:
the low setpoint value is lowered for the next working period, and
the high setpoint value is raised for the next working period.

According to one embodiment of the invention, the photosynthetic microorganism cells are cells of the species *Tisochrisis lutea*, preferably the *Tisochrisis lutea* CCAP 927/17 strain.

Other advantages and characteristics of the invention will emerge on reading the detailed description below and with reference to the appended drawings in which.

The drawings and the description below mostly contain elements of definite nature. They are an integral part of the description, and may thus not only serve to understand the present invention more clearly, but also contribute to its definition, where appropriate.

For a good production of microalgae (or microalgae biomass), said microalgae should be cultured in a culture medium rich in nutrients (nitrogen, phosphorus, sulfur, trace elements, vitamins) at temperature and pH values that are optimal for the microalgae, and sufficient light should be provided. The presence of the nutrients is necessary in order to allow the microalgae to convert the light energy by metabolizing $CO_2$. The result of this conversion is the production of oxygen and an increase in biomass through the proliferation of the microalgae (multiplication by cell division). After one or more working periods, a portion of the culture medium containing microalgae is removed from the tank, and fresh culture medium is poured into the tank. This is because, after one or more working periods, the nutrients of the culture medium are exhausted and the microalgae may secrete/produce toxic components. It is then advisable to eliminate a portion of the culture medium with a portion of the microalgae and to replace this portion with fresh culture medium. Conventionally, the culture medium is renewed proportionally relative to the growth rate of the microalgae cells (in this case preferably using a coefficient of proportionality equal to 1). In one embodiment, the method of the invention provides for a mean degree of renewal of the culture medium of approximately 10% over all of the working period(s).

Conventionally, a light source capable of emitting light at a wavelength which is highly absorbed by the microalgae is used, in order to obtain a high growth rate.

The publications *Light requirements in microalgal photobioreactors: an overview of biophotonic aspects*—Carvalho et al., Appl Microbiology and Biotechnology, 2011, vol. 89, no. 5: 1275-1288, *Light emitting diodes (LEDs)*

*applied to microalgal production*—Schulze et al., *Trends in Biotechnology*, 2014, vol. 32, no. 8: 422-430 and *Optimizing conditions for the continuous culture of Isochrysis affinis galbana relevant to commercial hatcheries*—Marchetti, Bourgaran & Dean, Aquaculture, 2012, 326/329, 106-105 describe the use of light in microalgae culture systems or the temperature and pH conditions for obtaining good cell growth as a function of the microalgae.

Figure 1:
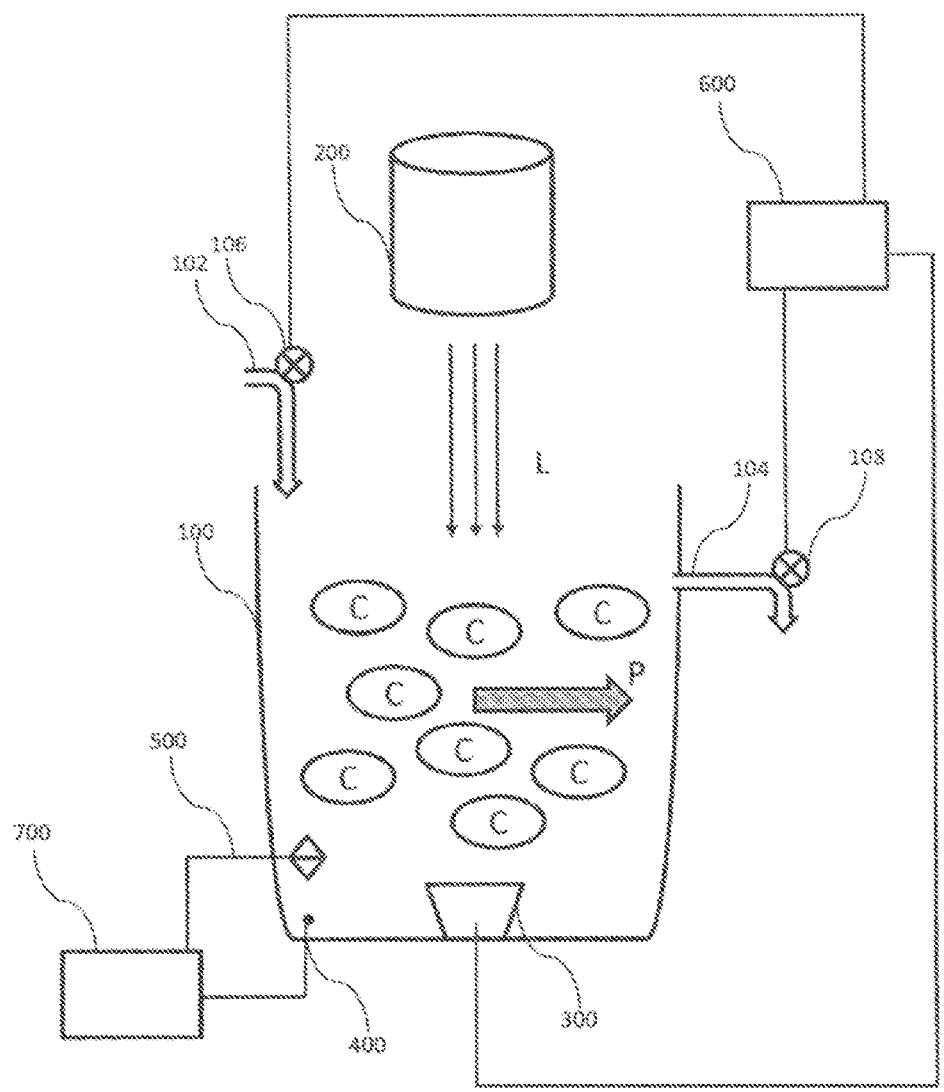
FIG. 1 shows a scheme for production of microalgae biomass in a bioreactor according to the invention.

FIG. 1 shows a scheme for production of microalgae biomass in a bioreactor of the invention operating in continuous mode. Continuous-mode bioreactors have the advantage of having a culture medium input and output, linked to a controller which makes it possible to operate the tank continuously at a chosen concentration of microalgae in the culture medium during a working period.

The bioreactor comprises a tank 100 capable of receiving a culture medium comprising microalgae. The microalgae are dispersed in the culture medium or are in the form of a biofilm. The microalgae consist of cells C of photosynthetic microorganisms. The bioreactor comprises an inlet 102 and an outlet 104 respectively linked to a device for adjusting the flow rate. Thus, the inlet 102 and the outlet 104 are respectively linked to a first valve (or pump) 106 and a second valve (or pump) 108 for opening and closing the inlet 102 and the outlet 104. The inlet 102 and the first valve 106 make it possible to control the introduction of the fresh culture medium into the tank 100. The outlet 104 and the second valve 108 make it possible to control the discharge of the culture medium and, where appropriate, of at least some of the cells C. The inlet and the outlet make it possible to continuously operate the bioreactor for a production P of microalgae biomass.

In general, the control of the biomass production in a continuous-mode culture system relies on controlling the cell growth of the microalgae culture. The concentration x [g/l] of microalgae in the culture medium changes as a function of the specific growth rate $\mu(x)$ [$h^{-1}$]. In continuous systems, the concentration also changes as a function of the dilution rate D [$h^{-1}$] of the culture medium. The dilution rate D is defined by the inlet flow rate (l/h) divided by the volume (l) of the culture medium.

The concentration x [g/l] of microalgae in the culture medium changes over time. For a given microalgae strain, this change can be expressed by the following formula F1:

$$\dot{x} = \mu x - Dx \quad [F1]$$

Consequently, for the production of biomass in the tank 100 of the bioreactor (at constant volume):

If $\mu(x) > D$: the cells multiply (by cell division) more quickly than they are discharged, their number and therefore their concentration (biomass) will increase.

If $\mu(x) < D$: the cells multiply (by cell division) less quickly than they are discharged, their number and therefore their concentration (biomass) will decrease.

If $\mu(x) = D$: the number of cells remains constant over time. The number of cells discharge with the culture medium from the tank is equal to the number of cells obtained by their multiplication in the culture medium inside the tank. The concentration is stable.

The bioreactor comprises a light source 200. The light source 200 is capable of emitting an incident light L. The light L is typically chosen to cover the entire solar spectrum including blue light (preferably from 430 nm to 470 nm) and red light (preferably from 650 nm to 700 nm). These wavelength ranges allow a good growth rate of the microalgae since they are highly absorbed by said microalgae.

The optical, absorbance and photon metabolization phenomena in a bioreactor tank are detailed in the handbooks *Microalgal biotechnology: potential and production*, C. Posten and C. Walter, de Gruyter, 2012 and *Handbook of Microalgal Culture: Applied Phycology and Biotechnology*, $2^{nd}$ edition, A. Richmond and Q. Hu, Wiley-Blackwell, 2013.

The cell concentration in the present invention is chosen so as to avoid problems linked to a light gradient (self-shadowing phenomenon). In general, the cell concentration $x_i$ is between 0.01 g/l and 5.0 g/l. Preferably, the concentration is approximately 0.1 g/l.

One objective of the present invention is to select and culture microalgae rich in substances of industrial interest. Thus, the applicant proposes a new selection method based on the induction of a heat stress on microalgae. The applicant has discovered, not without surprise, that, in a culture system, a particular scheme of successive temperature phases makes it possible to select and/or modify microalgae suitable for industrial exploitation. The system of the invention can be operated in continuous mode or in semi-continuous mode of fed-batch type.

Some microalgae species are capable of adapting to temperatures which do not correspond to the temperatures of their natural environment. Microalgae exposed to temperatures lower and/or higher than their optimal growth temperature can acclimatize by increasing their capacity to store certain metabolites. For example, some microalgae cells increase their capacity to store polar lipids rich in polyunsaturated fatty acids such as docosahexaenoic acid (DHA) and eicosapentaenoic acid (EPA) in response to heat stresses. These are products that are of great industrial interest.

The publication *Validation of a simple model accounting for light and temperature effect on microalgal growth*, Bernard & Rémand, Bioresource Technology, 2012, 123, 520-7 identifies critical temperatures for microalgae. This involves in particular an optimal growth temperature and also maximum and minimum temperatures above which the growth is inhibited. The difference between maximum and minimum growth temperature is referred to as thermal niche.

The prior art makes a distinction between microorganisms termed "thermal specialists" and microorganisms termed "thermal generalists", cf. *Evolution in changing environments*, Levins, Princeton Univ Press Princeton N.J., 1968, 2(2), 120; and *Hotter is better and broader: thermal sensitivity of fitness in a population of bacteriophages*, Knies et al., The American Naturalist, 2009, 173(4), 419-430. The thermal specialist microorganisms have a narrow thermal niche and a high growth rate. The thermal generalist microorganisms have a broad thermal niche and a low growth rate.

The approach of the applicant is radically opposed to the teaching of the prior art. Indeed, the applicant has discovered, not without surprise, that modifying the minimum and maximum growth temperatures (increasing the thermal niche) makes it possible to increase the growth rate of microalgae. The productivity and the yield are increased.

One objective of the invention is thus to generate new microalgae strains which have an increased content of products of industrial interest (enzymes, proteins, etc.). The invention makes it possible to obtain large biomasses of valuable cells of microalgae.

A heat stress results in cell death or, as appropriate, adaptation of the microalgae cells. This adaptation results in particular in genetic mutations in the microalgae cells. In other words, the natural genetic mutations induced by heat stress result in genetic adaptation mechanisms. Genetic mutations are able to be transmitted from one cell to its descendants, and thus to be transmitted from generation to generation.

A genetic mutation can, for example, result in an increase in membrane proteins or lipids in the microalgae cells. It can also result in the accumulation of metabolites in the cells. In this way, the microalgae become more resistant to temperature variations becoming distant from the optimal growth temperature.

Figure 2:
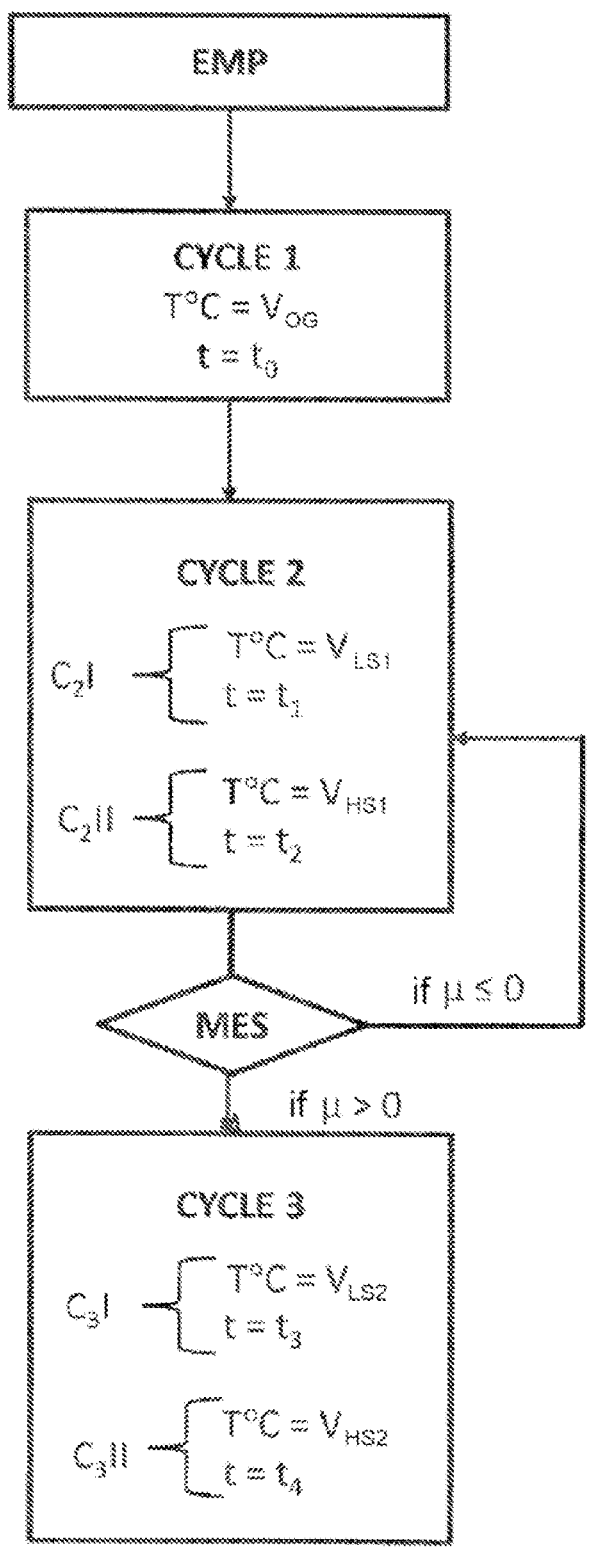
FIG. 2 shows a general flowchart of a selection method according to the invention.

FIG. 2 shows a general flowchart of a selection method according to the invention. An EMP operation comprises the provision of a cell culture of microalgae and of a nutritional culture medium suitable for the growth of the chosen culture. The operation comprises a suboperation which consists in filling the tank 100 with culture medium and inoculating this medium with the microalgae cells.

A CYCLE 1 operation comprises a microalgae growth phase under optimal growth conditions. To this effect, the temperature T° C. is adjusted to an optimal growth value $V_{OG}$. The optimal growth value $V_{OG}$ varies according to the microalgae species. The duration of the CYCLE 1 operation is variable. In general, a growth operation in the present invention lasts 24 hours. Each growth operation can be repeated. Thus, the CYCLE 1 operation can last for a period of time equal to 24 h ($t=t_0$). The CYCLE 1 operation can be repeated two to seven times for example. Thus, the CYCLE 1 operation can last between 48 h and 7 days.

The CYCLE 1 operation is followed by a CYCLE 2 operation of the invention. The CYCLE 2 operation comprises a first phase $C_2I$ in which the temperature is adjusted to a first low setpoint value $V_{LS1}$. The low setpoint value $V_{LS1}$ is to be chosen so as to satisfy temperature conditions that are colder compared with the optimal growth temperature conditions ($V_{LS1}<V_{OG}$). Thus, the low setpoint value induces a heat stress on the microalgae. The first phase $C_2I$ is maintained for a predefined period of time $t=t_1$.

The CYCLE 2 operation comprises a second phase $C_2II$ in which the temperature is adjusted to a first high setpoint value ($V_{HS1}$). The high setpoint value $V_{HS1}$ is to be chosen so as to satisfy temperature conditions that are hotter compared with the optimal growth temperature conditions ($V_{HS1}>V_{OG}$). Thus, the high setpoint value induces a heat stress on the microalgae. The second phase $C_2II$ is maintained for a predefined period of time $t=t_2$.

The respective durations of the first and second phases are chosen such that $t_1+t_2=24$ hours. The succession of the first and second phases can be repeated seven times for example. Thus, the CYCLE 2 operation can last between 7 days.

Figure 3:
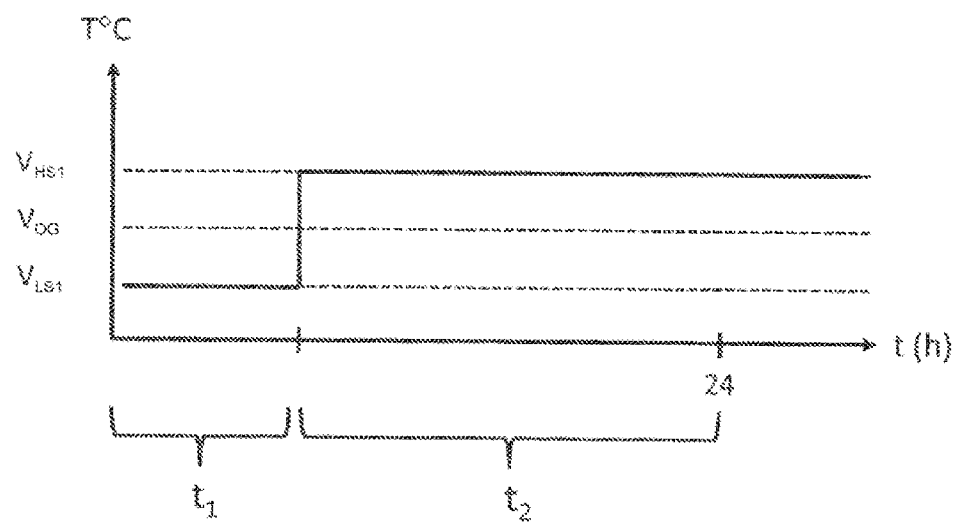
FIG. 3 shows a change in the temperature during a working period of the method of the invention.

FIG. 3 shows the change in the temperature during the CYCLE 2 operation as a function of time, over a period of 24 hours.

The CYCLE 2 operation is followed by an MES operation of measuring the specific growth rate μ of the microalgae. If μ is less than or equal to zero, the CYCLE 2 operation is repeated; if μ is greater than zero, a subsequent CYCLE 3 operation is initiated.

The CYCLE 3 operation comprises a first phase $C_3I$ in which the temperature is adjusted to a second low setpoint value ($V_{LS2}$). The low setpoint value $V_{LS2}$ is to be chosen so as to satisfy temperature conditions that are colder compared with the first low setpoint value in the CYCLE 2 operation ($V_{LS2}<V_{LS1}$). The second low setpoint value induces a heat stress on the microalgae. The first phase $C_3I$ is maintained for a predefined period of time $t=t_3$.

The CYCLE 3 operation comprises a second phase $C_3II$ in which the temperature is adjusted to a second high setpoint value $V_{HS2}$. The second high setpoint value $V_{HS2}$ is to be chosen so as to satisfy temperature conditions which are hotter compared with the first high setpoint value in the CYCLE 2 operation ($V_{HS2}>V_{HS1}$). The high setpoint value induces a heat stress on the microalgae. The second phase $C_3II$ is maintained for a predefined period of time $t=t_4$.

The respective durations of the first and second phases are chosen so that $t_3+t_4=24$ hours. The succession of the first and second phases can be repeated seven times for example. Thus, the CYCLE 3 operation can last between 7 days.

Figure 4:
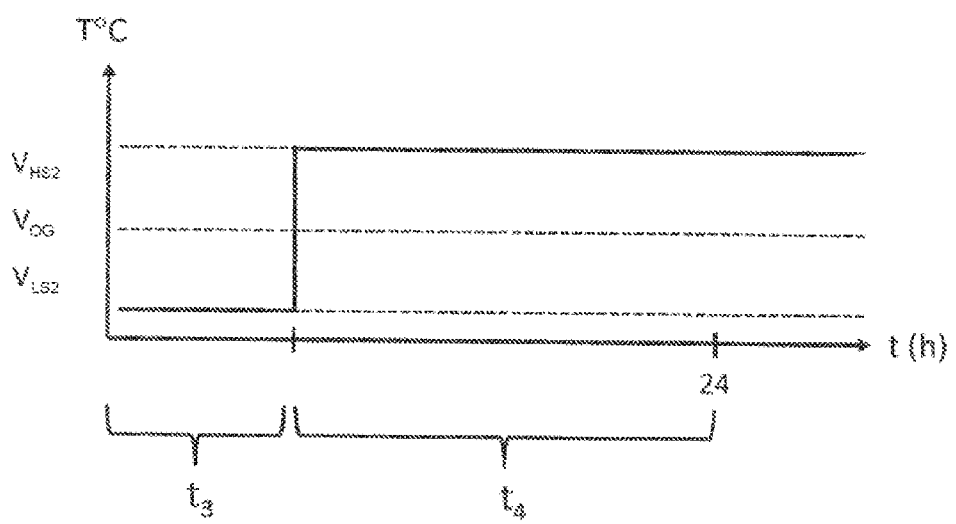
FIG. 4 shows a change in the temperature during another working period of the method of the invention.

FIG. 4 shows the change in the temperature during the CYCLE 3 operation as a function of time, over a period of 24 hours.

The scheme of the successive operations (in this case: CYCLE 2, then MES, then CYCLE 3) above can be repeated a predefined number of times, for example as a function of the microalgae species.

Thus, the CYCLE 3 operation can be followed by a new operation of measuring the specific growth rate p of the microalgae. If p is less than or equal to zero, the CYCLE 3 operation can be repeated; if p is greater than zero, a subsequent CYCLE 4 operation can be initiated. The CYCLE 4 operation then comprises low and high setpoint values respectively below and above the setpoint values of the CYCLE 3 operation. This will induce heat stresses on the microalgae cells.

Exemplary Embodiment

The bioreactor of the present embodiment comprises a tank 100 with a culture medium. The culture medium comprises a dispersion of a cell culture of photosynthetic microorganisms.

The chosen starting cell culture of photosynthetic microorganisms is the microalgae strain *Tisochrisis lutea* CCAP 927/17. In the remainder of the present description, this strain is referred to as W2X.

The initial W2X strain exhibits a good triglyceride productivity, cf. Bougaran et al. *Enhancement of neutral lipid productivity in the microalga Isochrysis affinis Galbana (T-Iso) by a mutation-selection procedure*, Biotechnology and Bioengineering, 2012, 109(11), 2737-45 and Carrier et al. *Comparative transcriptome of wild type and selected strains of the microalgae Tisochrysis lutea provides insights into the genetic basis, lipid metabolism and the life cycle*, PLoS ONE, 2014, 9(1).

The tank has a volume capacity of 1.9 l. In this case, the culture medium is of f/2 type, cf. *Culture of phytoplankton for feeding marine invertebrates*, Culture of Marine Invertebrate Animals—Plenum, 1975. The tank 100 also comprises means for mixing the culture medium. In this case, it involves a magnetic stirrer and a blower (of air-pump type) capable of generating fine bubbles in the culture medium. The bioreactor comprises an inlet 102 and an outlet 104. The inlet 102 makes it possible to introduce fresh culture medium into the tank 100. The outlet 104 makes it possible to discharge culture medium and microalgae from the tank 100. The inlet 102 and the outlet 104 are linked to a controller. The controller makes it possible to operate the tank 100 in continuous mode for a working period. The working period varies according to the microalgae strains present in the culture medium. The working period preferentially extends at least to one month (without upper time limit), which generally corresponds to at least 20 microalgae generations (that is to say 20 successive cell divisions). According to the invention, the working period is greater than the time required for a microalgae cell cycle (cell division). In the present embodiment, the working period is 260 days. Advantageously, the tank of the bioreactor is regularly cleaned (for example each month). The cleaning can be carried out by means of 70% ethanol followed by washing with hydrochloric acid (HCl), and rinsing with fresh culture medium. During the cleaning of the tank, the culture medium comprising the cell culture is kept under sterile conditions.

The bioreactor comprises a light source 200 which emits an incident light L having an incoming light intensity $I_{in}$ sufficiently high to pass through the tank 100 filled with the culture medium comprising the microalgae dispersion. The light source 200 is capable of emitting an incoming light intensity $I_{in}$ which can range up to 5000 µmol quanta m$^{-2}$ s$^{-1}$. In the present embodiment, the light source is arranged to emit a fixed intensity of 250 µmol quanta m$^{-2}$ s$^{-1}$. The light source 200 emits a constant value of incoming intensity $I_{in}$ during the working period. In this case, the light source comprises light-emitting diodes from the company *Nichia Corporation*, of *NVSL219BT* 2 700° K. type. A controller 600 operates the tank 100 in continuous mode at a dilution rate D. For this, the controller 600 comprises one or more light sensors 300, such as photoelectric cells, for measuring the optical density of the culture medium/microalgae combination in the tank 100. In this way, the controller 600 can maintain the cell culture concentration $x_i$ in the culture medium at a chosen value, for example approximately 1.0 g/l, during the working period. The controller is arranged to adjust the dilution rate D by introducing and discharging culture medium. A concentration of approximately 1.0 g/l allows good light scattering in the tank 100. In this case, the bioreactor comprises a light sensor 300 from the company Skye Instruments of SKL2620 type.

In the present exemplary embodiment, the selection protocol of the invention is carried out in a continuous-mode bioreactor. The turbidity is kept constant at approximately 9×10$^5$ cells/ml. This is carried out by a continuous measurement at 800 nm by the sensor 300 and an operation by adjustment of dilution by the controller 600. Reference is made here to the "SFturb" selection mode.

In parallel, the selection protocol of the invention is carried out in a fed-batch bioreactor. A dilution using fresh culture medium is carried out every seven days; 5% to 10% of the culture medium/microalgae cell mixture is stored before the dilution. The initial cell concentration after dilution is thus approximately 5×10$^3$ cells/l. Reference is made here to the "SFb" selection mode.

The pH of the culture medium comprising microalgae is maintained at pH=8.2 by addition of carbon dioxide ($CO_2$) during the working period.

The bioreactor also comprises a temperature regulator 500 capable of increasing and decreasing the temperature of said culture medium in the tank. In this case, the regulator comprises a system for cooling/heating carried out by means of a water jacket placed around the periphery of the tank 100. The bioreactor comprises a temperature probe 400 for measuring the temperature of said culture medium in the tank. The bioreactor also comprises a control 700 of the temperature regulator 500 arranged to adjust, during a first period, the temperature of the culture medium to a low setpoint value $V_{LS}$, and during a second period, the temperature of the culture medium to a high setpoint value $V_{HS}$, the succession of said first and second periods making it possible to induce a cellular stress in at least some of said photosynthetic microorganisms during the working period. In this case, the control 700 comprises a thermostat from the company Lauda Brinkmann of Proline RP 845 type.

The adjustment of the temperature with a view to reaching the high and low setpoint temperatures can be carried out in various ways by the control. Thus, the decreasing and/or the increasing of the temperature can in particular be carried out linearly, exponentially, or stepwise.

According to the invention, the mean temperature $T_M$ of the culture medium (and thus received per microalgae cell) is kept constant during the working period. This is radically different than the prior art approaches which aim to gradually increase the mean temperature received per cell. The control 700 is arranged to satisfy the following mean temperature condition during the working period:

$$TM = \frac{(VLS \times \text{first period}) + (VHS \times \text{second period})}{\text{working period}}$$

The amplitude (or difference) between the low setpoint and high setpoint values is increased from one cycle to the next (or from one working period to the next).

The present selection protocol provides for cycles of temperature variation every 24 hours.

The optimal growth temperature $T_{opt}$ (temperature value $V_{OG}$) for the W2X strain (*Tisochrisis lutea* CCAP 927/17) is equal to 28° C. The chosen mean temperature over 24 hours in the present exemplary embodiment is equal to 28° C.

Each cycle (working period) comprises a first period for which the temperature of the culture medium is adjusted to a temperature $T_{low}$ that is colder than the optimal growth temperature. The control adjusts the temperature to the low setpoint value $V_{LS}$. In the present embodiment, the first period is 8 hours. Each cycle (working period) also comprises a second period for which the temperature of the culture medium is adjusted to a temperature $T_{high}$ that is hotter than the optimal growth temperature. The control adjusts the temperature to the high setpoint value $V_{HS}$. In the present embodiment, the second period is 16 hours.

The succession of said first and second periods makes it possible to induce a cellular stress in at least some of said cells of the W2X strain.

In the 1$^{st}$ selection cycle, the low setpoint value $V_{LS}$ ($T_{low}$) is equal to 26° C. In the 1$^{st}$ selection cycle, the high setpoint value $V_{HS}$ ($T_{high}$) is equal to 29° C.

Thus, the microalgae are exposed for 8 hours at 26° C., followed by 16 hours at 29° C. The mean temperature received by the microalgae over the course of 24 hours is equal to 28° C. ($T_{opt}$).

The 1$^{st}$ selection cycle is repeated for 7 days. After 7 days, the growth rate µ is determined. If µ is less than or equal to zero, the temperature conditions of the 1$^{st}$ selection cycle are repeated identically; if p is greater than zero, a 2$^{nd}$ selection cycle is initiated.

In the 2$^{nd}$ selection cycle, the low setpoint value $V_{LS}$ ($T_{low}$) is equal to 24° C. In the 2$^{nd}$ selection cycle, the high setpoint value $V_{HS}$ ($T_{high}$) is equal to 30° C.

Thus, the microalgae are exposed for 8 hours at 24° C., followed by 16 hours at 30° C. The mean temperature received by the microalgae over the course of 24 hours is equal to 28° C. ($T_{opt}$).

The 2$^{nd}$ selection cycle is repeated for 7 days. After 7 days, the growth rate µ is determined. If µ is less than or equal to zero, the temperature conditions of the 2$^{nd}$ selection cycle are repeated; if µ is greater than zero, a 3$^{rd}$ selection cycle is initiated.

Each subsequent cycle (or working period) lowers, on the one hand, the low setpoint value $V_{LS}$ ($T_{low}$) by 0.5° C. to 1°

C., and increases, on the other hand, the high setpoint value $V_{HS}$ ($T_{high}$) by 0.25° C. to 0.5° C., while the first and second periods remain identical (respectively, 8 hours and 16 hours).

The temperature conditions are increasingly extreme from one working period to another. Thus, the low setpoint value $V_{LS}$ ($T_{low}$) can for example reach 12° C. and the high setpoint value $V_{HS}$ ($T_{high}$) can for example reach 36° C. The selection is increasingly strict while increasing the number of successive working periods.

In the present exemplary embodiment, the working period of 24 hours is repeated 259 times (total of 260 days).

As a variant, it is possible to modify the first and second periods. For example, in one embodiment, the first period is fixed at 6 hours and the second period is fixed at 12 hours. A third period is then provided for, during which the temperature is kept equal to the optimal growth value ($V_{OG}$). Thus, the mean temperature received by the microalgae remains constant over the course of 24 hours. By way of example, mention may be made of a selection cycle in which:

- the temperature $T_{low}$ at the low setpoint value $V_{LS}$ equal to 26° C. is maintained for 6 hours;
- the temperature $T_{high}$ at the high setpoint value $V_{HS}$ equal to 29° C. is maintained for 12 hours, and in which
- the temperature $T_{opt}$ at the optimal growth value $V_{OG}$ equal to 28° C. is maintained during a third period equal to 6 hours.

The mean temperature received per microalgae cell over the course of 24 hours is then equal to 28° C. ($T_{opt}$).

In this variant, the general premise in which, for a given (predefined) working period, the second period lasts twice as long (double) as the first period, is verified. A third period is added thereto in order to supplement said given working period.

Figure 5:
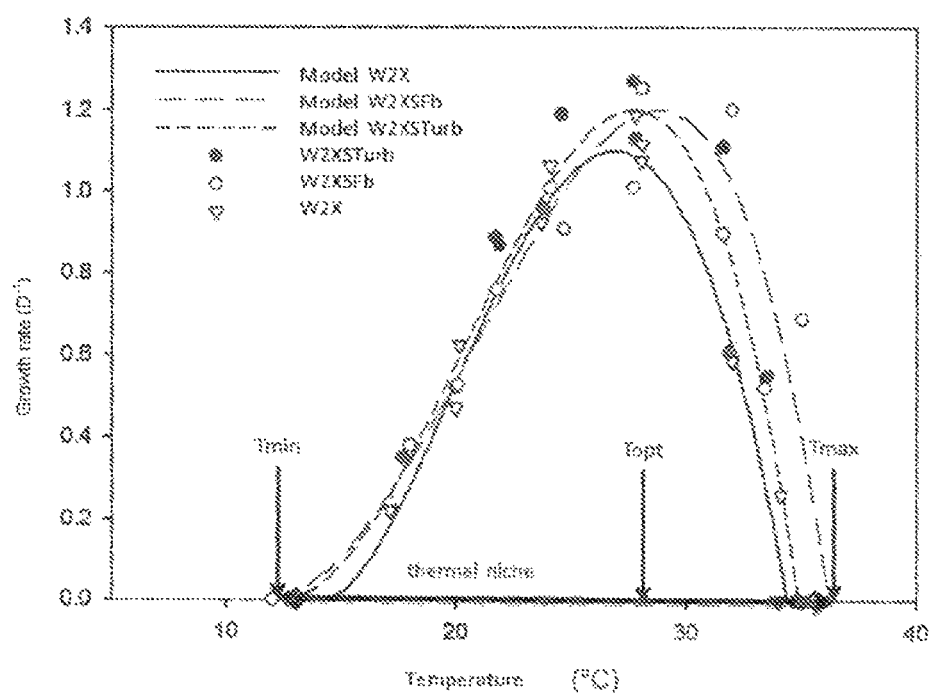
FIG. 5 shows a comparative diagram of thermal niches between a microalgae strain of the prior art and two microalgae strains selected and/or modified according to the invention.

FIG. 5 shows the growth rate per day ($d^{-1}$) relative to the temperature (° C.) of the initial W2X strain and of the W2X strains having been subjected to the selection protocol of the invention, namely, respectively, W2XSTurb (for the W2X strain selected in the continuous-mode bioreactor) and W2XSFb (for the W2X strain selected in the fed-batch bioreactor). FIG. 5 shows that the thermal niche of the adapted strains W2XSTurb and W2XSFb is increased compared with the initial W2X strain. The extreme temperatures, namely the minimum growth temperatures $T_{min}$ and the maximum growth temperatures $T_{max}$ for each strain were calculated according to the model proposed in *Validation of a simple model accounting for light and temperature effect on microalgal growth*, Bernard & Rémand, Bioresource Technology, 2012, 123, 520-7.

Figure 6:
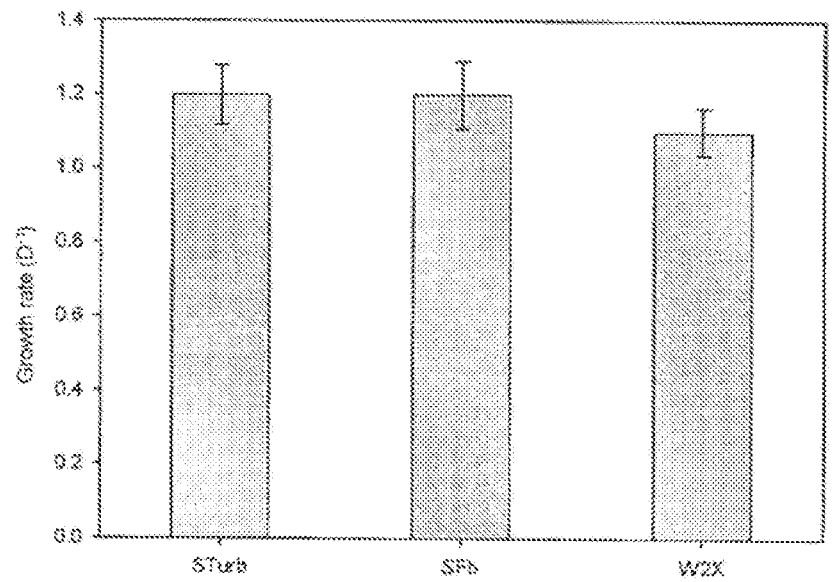
FIG. 6 shows a comparative diagram of the growth rate between a microalgae strain of the prior art and two microalgae strains selected and/or modified according to the invention.

FIG. 6 shows a comparative diagram between the initial W2X strain and the strains modified by the method of the invention, W2XSFb and W2XSTurb. The strains generated according to the invention have an increased growth rate compared with the initial W2X strain.

Figure 7:
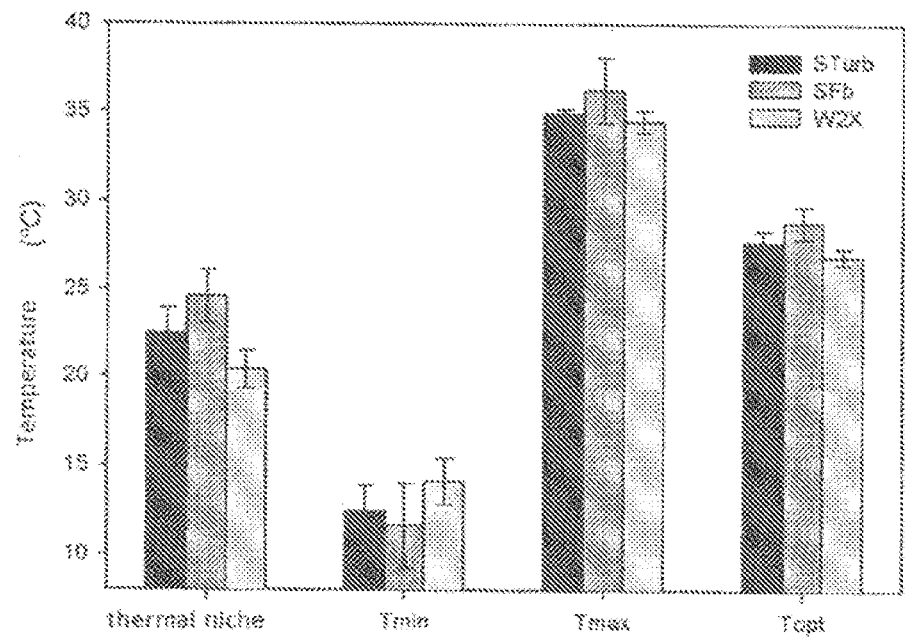
FIG. 7 shows a comparative diagram of growth temperatures and thermal niches between a microalgae strain of the prior art and two microalgae strains selected and/or modified according to the invention.

FIG. 7 shows a comparative diagram of the W2X, W2XSFb and W2XSTurb strains between the minimum growth temperatures $T_{min}$, the maximum growth temperatures $T_{max}$, the optimal growth temperature $T_{opt}$ and the thermal niches.

FIGS. 5 and 6 show that the growth rates of the adapted strains W2XSTurb and W2XSFb are higher than the growth rate of the initial W2X strain. FIG. 7 shows that the thermal niches of the adapted strains W2XSTurb and W2XSFb are broader than the thermal niche of the initial W2X strain. Thus, FIGS. 5 to 7 demonstrate that the microalgae modified by means of the selection method of the invention have a high growth rate and a broadened thermal niche. This is contrary to the results and models of the prior art which associate a broad thermal niche with a low growth rate. The advantage for an industrial exploitation of the adapted strains W2XSTurb and W2XSFb is increased compared with the initial W2X strain which has a narrower thermal niche.

Figure 8:
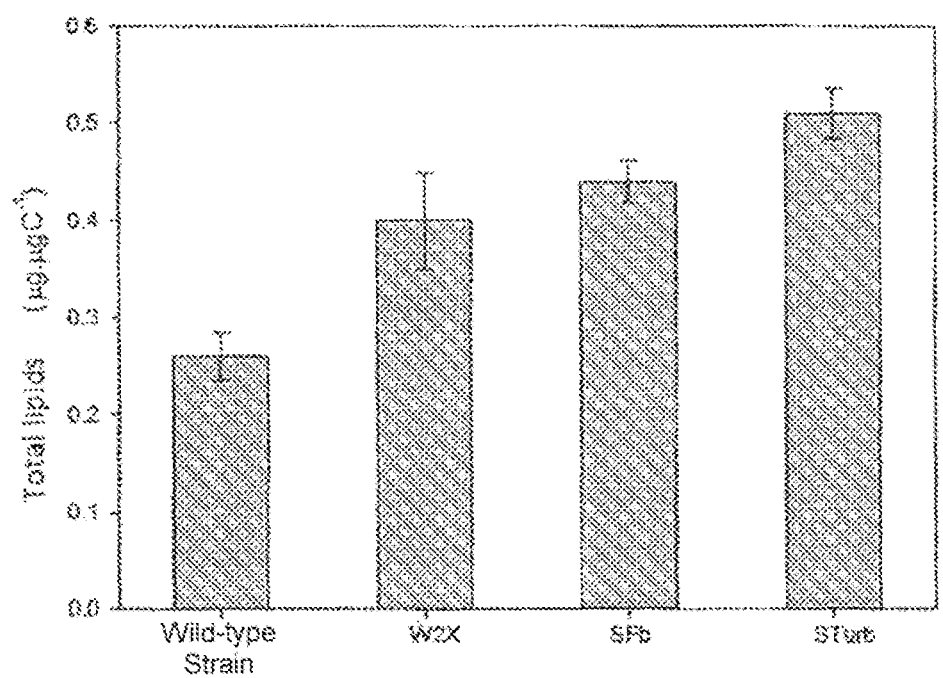
FIG. 8 shows a comparative diagram of the total content of lipids present in the strains obtained according to the invention and of strains of the prior art.

FIG. 8 shows a comparative diagram of the total content of lipids present in a wild-type *Tisochrisis lutea* strain, namely the CCAP 927/14 strain (cf. Bougaran et al. *Enhancement of neutral lipid productivity in the microalga Isochrysis affinis Galbana (T-Iso) by a mutation-selection procedure*, Biotechnology and Bioengineering, 2012, 109 (11), 2737-45), in the initial W2X strain, in the W2XSFb strain and in the W2XSTurb strain. The strains modified by the method of the invention, W2XSFb and W2XSTurb, have increased lipid contents (μg of lipids per μg of algae carbon) compared with the wild-type strain and the initial W2X strain.

The fatty acids and their respective content, contained in the samples of the initial W2X strain, of the W2XSFb strain and of the W2XSTurb strain, were identified by gas chromatography (GC). The fatty acid composition and the respective amounts of these acids were determined. Table 1 shows the results.

TABLE 1

Comparison of the fatty acid compositions of the adapted strains W2XSFb and W2XSTurb and the initial fatty acid composition in the W2X strain

| Fatty acid | W2XSTurb [1st Sample] | W2XSTurb [2nd Sample] | W2XSFb | W2X |
|---|---|---|---|---|
| Saturated fatty acids: | | | | |
| C14:0 | 24.70 | 24.24 | 21.73 | 22.1 |
| C15:0 | 0.32 | 0.33 | 0.29 | |
| C16:0 | 14.21 | 14.12 | 14.57 | 16.9 |
| C18:0 | 0.50 | 0.54 | 0.79 | 0.7 |
| Total | 40.47 | 39.93 | 38.071 | 39.9 |
| Monounsaturated fatty acids: Monoene | | | | |
| C14:1n-5 | 0.55 | 0.63 | 0.45 | |
| C16:1n-7 | 2.28 | 2.09 | 2.56 | 5.1 |
| C18:1n-9 | 21.71 | 22.99 | 22.99 | 28.9 |
| C18:1n-7 | 1.282 | 1.29 | 1.70 | 1.1 |
| Total | 27.60 | 29.23 | 29.87 | 37.9 |
| Polyunsaturated fatty acids: Diene | | | | |
| C16:2n-6 | 0.13 | 0.12 | 0.15 | 0.1 |
| C16:2n-4 | 0.31 | 0.31 | 0.41 | 0.2 |
| C18:2n-6 | 4.41 | 4.97 | 3.45 | 3.8 |
| C20:2n-6 | 0.064 | 0.081 | 0.13 | 0.1 |
| Triene | | | | |
| C18:3n-3 | 3.81 | 3.891 | 4.63 | 3.1 |
| C20:3n-6 | 0.0531 | 0.049 | 0.079 | 0.1 |
| C20:3n-3 | 0.0351 | 0.031 | 0.092 | 0.2 |
| Tetraene | | | | |
| C18:4n-3 | 7.746 | 7.25 | 9.70 | 6.8 |
| C20:4n-6 | 0.072 | 0.10 | 0.089 | 0.1 |
| C20:4n-3 | 0.024 | 0.0031 | 0.020 | 0.3 |
| Pentaene | | | | |
| C18:5n-3 | 0.65 | 0.59 | 0.76 | 0.4 |
| C20:5n-3 (EPA) | 0.24 | 0.23 | 0.21 | 0.2 |

TABLE 1-continued

Comparison of the fatty acid compositions of the adapted strains W2XSFb and W2XSTurb and the initial fatty acid composition in the W2X strain

| Fatty acid | W2XSTurb [1st Sample] | W2XSTurb [2nd Sample] | W2XSFb | W2X |
|---|---|---|---|---|
| C22:5n-6 | 2.16 | 2.06 | 1.94 | 0.8 |
| C22:5n-3 | 0.095 | 0.14 | 0.33 | 0.9 |
| C22:6n-3 (DHA) | 11.39 | 10.21 | 9.32 | 5 |
| Total Poly | 31.92 | 30.83 | 32.06 | 22.4 |

The results appearing in table 1 show that the microalgae strains adapted (in particular genetically modified) by the method of the invention have increased amounts of fatty acids. Most particularly, a significant increase is observed for DHA which is of great industrial value.

The modification of the W2X strain by means of the bioreactor of the invention results in modified strains of W2X (in this case W2XSFb and W2XSTurb) having a thermal niche increased by several degrees Celsius (in this case up to 3° C.). The W2X strains modified according to the invention also have an increased fatty acid content compared with the initial W2X strain (in particular in terms of DHA). The growth rate of the W2X strains modified according to the invention is increased compared with the initial W2X strain.

The invention claimed is:

1. A bioreactor characterized in that it comprises a tank capable of being operated during a working period, and capable of repeating the working period once it has been completed, said tank being intended to receive a culture medium comprising a cell culture of photosynthetic microorganisms, a light source arranged to emit incident light having a chosen incoming light intensity ($I_{in}$) in the direction of the tank, a temperature probe for measuring the temperature of said culture medium in the tank, and a temperature regulator capable of increasing and decreasing the temperature of said culture medium in the tank, and in that the tank also comprises a control of the temperature regulator arranged to adjust the temperature of the culture medium to a low setpoint value ($V_{LS}$) during a first period, and to adjust the temperature of the culture medium to a high setpoint value ($V_{HS}$) during a second period, the succession of said first and second periods making it possible to induce a cellular stress in at least some of said photosynthetic microorganisms during the working period, and wherein the control is also arranged to receive data relating to the growth rate of said cell culture of photosynthetic microorganisms after each working period of a plurality of working periods, and wherein the control fixes the low setpoint value and said high setpoint value for a subsequent working period after said reception of the data relating to the growth rate of said cell culture of photosynthetic microorganisms from a prior working period, and wherein the control is arranged to determine said low setpoint value and said high setpoint value and said first and second periods so as to maintain a mean setpoint value ($V_M$) during each working period, the mean value being equal to the sum of the product of said low setpoint value and of said first period and of the product of said high setpoint value and of said second period, divided by the working period, and wherein the plurality of working periods includes more than two working periods so as to bring about a cellular degradation of at least one portion of said photosynthetic microorganisms and thus to select the photosynthetic microorganisms having valuable properties.

2. The bioreactor according to claim 1, wherein said mean setpoint value is substantially equal to the optimal growth temperature ($T_{opt}$) of the cell culture of photosynthetic microorganisms.

3. The bioreactor according to claim 1, wherein said chosen incoming light intensity ($I_{in}$) of the incident light is fixed during the working period.

4. The bioreactor according to claim 1, wherein said chosen incoming light intensity ($I_{in}$) of the incident light is between 100 and 2000 µmol quanta m$^{-2}$ s$^{-1}$.

5. The bioreactor according to claim 1, also comprising a controller arranged to operate the tank at a chosen cell culture concentration ($x_i$), in the culture medium during said working period.

6. The bioreactor according to claim 1, also comprising a light sensor facing the light source, the sensor being capable of measuring an outgoing light intensity ($I_{out}$) and of transmitting data relating to this intensity ($I_{out}$) to the controller in order to calculate the concentration of the cell culture and to operate the tank at said chosen cell culture concentration ($x_i$) in the culture medium during the working period.

7. The bioreactor according to claim 1, also comprising a controller arranged to operate the tank at a cell culture concentration ($x_i$) substantially less than or equal to 1.0 g/l in the culture medium during said working period.

8. The bioreactor according to claim 1, wherein said chosen incoming light intensity ($I_{in}$) of the incident light is equal to approximately 250 µmol quanta m$^{-2}$ s$^{-1}$.

9. A method for selecting photosynthetic microorganisms, comprising the following steps:
   1. Providing a bioreactor according to claim 1;
   2. Filling the tank with a culture medium;
   3. Inoculating the culture medium with a cell culture consisting of photosynthetic microorganisms;
   4. Operating the tank during a working period and adjusting the incoming light intensity ($I_{in}$) to a chosen value;
   5. Adjusting the temperature of the culture medium to a low setpoint value ($V_LS$) during a first period, and adjusting the temperature of the culture medium to a high setpoint value ($V_{HS}$) during a second period, the succession of said first and second periods making it possible to induce a cellular stress in at least some of said photosynthetic microorganisms during the working period;
   6. Harvesting the photosynthetic microorganisms, and wherein the temperature adjustment step 5. is repeated more than two times so as to bring about a cellular degradation of at least one portion of said photosynthetic microorganisms and thus to select the photosynthetic microorganisms having valuable properties.

10. The method according to claim 9, wherein said low setpoint value and said high setpoint value and said first and second periods are adjusted so as to maintain a mean setpoint value ($V_M$) during the working period, the mean value being equal to the sum of the product of said low setpoint value and of said first period and of the product of said high setpoint value and of said second period, divided by the working period.

11. The method according to claim 9, wherein said mean setpoint value is substantially equal to the optimal growth temperature ($T_{opt}$) of the cell culture of photosynthetic microorganisms.

12. The method according to claim 9, also comprising the following steps:
   4a. Taking a portion of the culture medium comprising at least one portion of said photosynthetic microorganisms; and 4b. Compensating for said portion of the culture medium comprising at least one portion of said photosynthetic microorganisms taken, with fresh culture medium.

13. The method according to claim 9, wherein the harvesting in step 6. is carried out when the culture medium comprises a cell culture of photosynthetic microorganisms consisting of more than 75% of photosynthetic microorganisms having valuable properties.

14. The method according to claim 13, also comprising the following steps:
   7. Inoculating a fresh culture medium with the photosynthetic microorganisms having valuable properties in a bioreactor; and
   8. Operating the bioreactor of step 7. for a production of biomass consisting of said photosynthetic microorganisms having valuable properties.

15. The method according to claim 9, wherein the harvesting in step 6. is carried out when the culture medium comprises a cell culture of photosynthetic microorganisms consisting of more than 90% of photosynthetic microorganisms having valuable properties.

16. The method according to claim 9, wherein the harvesting in step 6. is carried out when the culture medium comprises a cell culture of photosynthetic microorganisms consisting of substantially 100% of photosynthetic microorganisms having valuable properties.

* * * * *